United States Patent
Nandi et al.

(10) Patent No.: US 10,851,036 B2
(45) Date of Patent: Dec. 1, 2020

(54) CATALYTIC PARTIAL OXIDATION OF METHANE

(71) Applicant: ExxonMobil Research and Engineering Company, Annandale, NJ (US)

(72) Inventors: Partha Nandi, Annandale, NJ (US); Steven L. Suib, Storrs, CT (US); Sumathy Raman, Annandale, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 16/203,920

(22) Filed: Nov. 29, 2018

(65) Prior Publication Data

US 2019/0185397 A1    Jun. 20, 2019

Related U.S. Application Data

(60) Provisional application No. 62/598,600, filed on Dec. 14, 2017.

(51) Int. Cl.
*C07C 29/50* (2006.01)
*C07C 29/52* (2006.01)

(52) U.S. Cl.
CPC ............. *C07C 29/50* (2013.01); *C07C 29/52* (2013.01)

(58) Field of Classification Search
CPC ................................ C07C 29/50; C07C 29/52
See application file for complete search history.

(56) References Cited

U.S. PATENT DOCUMENTS

| | | | | |
|---|---|---|---|---|
| 3,228,849 A * | 1/1966 | Fellows | ................... | G21C 3/64 376/323 |
| 2013/0236940 A1 * | 9/2013 | Reetz | ................... | C12N 9/0071 435/160 |
| 2015/0099876 A1 | 4/2015 | Chan et al. | | |
| 2018/0297976 A1 * | 10/2018 | Caradonna | ............... | B01J 31/18 |

* cited by examiner

*Primary Examiner* — Rosalynd A Keys
(74) *Attorney, Agent, or Firm* — Liza Negron

(57) ABSTRACT

Systems and methods are provided for direct methane conversion to methanol. The methods can include exposing methane to an oxidant, such as $O_2$, in a solvent at conditions that are substantially supercritical for the solvent while having a temperature of about 310° C. or less, or about 300° C. or less, or about 290° C. or less. The solvent can correspond to an electron donor solvent that, when in a supercritical state, can complex with $O_2$. By forming a complex with the $O_2$, the supercritical electron donor solvent can facilitate conversion of methane to methanol at short residence times while reducing or minimizing further oxidation of the methanol to other products.

19 Claims, No Drawings

CATALYTIC PARTIAL OXIDATION OF METHANE

CROSS-REFERENCE TO RELATED APPLICATIONS

This application claims the benefit of U.S. Provisional Application No. 62/598,600, filed on Dec. 14, 2017, the entire contents of which are incorporated herein by reference

FIELD

Embodiments of the invention relate to catalytic partial oxidation of methane to methanol.

BACKGROUND

The ability to directly convert methane to methanol is strongly desirable from an economic perspective. Current natural gas supplies can typically include about 95% of $CH_4$. Unfortunately, transportation of natural gas is roughly twice as expensive as transport of typical liquid fuels. Such transport costs can account for up to 40% to 80% of the price of natural gas and/or methane.

Thermodynamically, the partial oxidation of methane to methanol appears to be a favorable reaction. It has been a challenge, however, to directly oxidize methane with air as an oxidant. The C—H bond in methane is stronger than the C—H bond strength of methanol. Hence it has been impossible using conventional methods to stop the oxidation reaction at the stage of partial oxidation to methanol in any significant yield. Instead, further oxidation of methanol to formaldehyde, formic acid, CO and $CO_2$ happens readily in conventional gas phase reactors.

Alternatively, in a large capital intensive process involving an indirect conversion reaction pathway, methane can be converted into syngas which can subsequently be converted into either methanol or to a mix of hydrocarbons (Gas to Liquid or GTL plant) via a Fischer-Tropsch process. While this type of indirect method can be effective for conversion of methane to methanol, the capital-intensive nature of the process can substantially reduce the benefit of being able to convert the methane to methanol and/or other products. For example, indirect conversion of methane to methanol typically involves multiple reactions requiring distinct high temperature, high pressure environments. Maintaining each reaction environment at the correct temperature and/or pressure to perform the net conversion reaction can require substantial resources. A new alternative to directly convert methane to methanol remains an unmet need in this area.

U.S. Patent Application Publication No. 2015/0099876 describes a method for oxidizing hydrocarbons based on molecular catalysts. The method involves exposing a hydrocarbon to a tri-copper cluster catalyst in the presence of hydrogen peroxide in an acetonitrile solvent. The hydrogen peroxide is consumed during the reaction cycle. Although methane is described as a potential hydrocarbon for oxidation, only a modest conversion for oxidation of methane to methanol is shown in the examples. A method that can provide oxidation of methane to methanol with improved conversion rates and/or that can avoid the need for hydrogen peroxide as a reagent would be desirable. More generally, a process that can reduce or minimize the need for specialized catalysts and/or the need for reagents that are comparable to or more expensive than methane is desirable.

SUMMARY

In one aspect, a method for partial oxidation of methane is provided. The method includes contacting methane with $O_2$ in the presence of a solvent in a reaction environment under supercritical conditions for the solvent to form methanol. The supercritical conditions can include a temperature of 310° C. or less. The solvent can correspond to an electron donor solvent, such as acetonitrile and/or carbon dioxide. The residence time for exposure of the $O_2$ to the methane under supercritical (and/or substantially supercritical) conditions can be 0.1 seconds or more and/or 10 minutes or less. Optionally, the supercritical conditions can include a temperature of 300° C. or less, or 290° C. or less.

Optionally, the reaction environment can include a limited amount of water, such as 10 mole % or less of the components in the reaction environment. Additionally or alternately, the molar ratio of solvent to $O_2$ can be 5.0 or more. Additionally or alternately, the molar ratio of methane to $O_2$ can be 2.0 or more. Depending on the aspect, $C_{2+}$ hydrocarbons can also be present in the reaction environment, or the reaction environment can be substantially free of $C_{2+}$ hydrocarbons.

In some aspects, the yield of methanol can be 1.0 mole % or more relative to the molar amount of $O_2$ in the reaction environment. Additionally or alternately, the yield of methanol can be 0.7 mole % or more relative to the molar amount of $CH_4$ in the reaction environment.

Optionally, the methane can be contacted with the $O_2$ in the presence of an initiator, such as hydrogen peroxide or boron nitride.

Optionally, the selectivity for $CO_2$ can be 50 mole % or less relative to total moles of conversion products.

DETAILED DESCRIPTION

In various aspects, systems and methods are provided for direct methane conversion to methanol. The methods can include exposing methane to an oxidant, such as $O_2$, in a solvent at conditions that are substantially supercritical for the solvent while having a temperature of about 310° C. or less, or about 300° C. or less, or about 290° C. or less. The solvent can correspond to an electron donor solvent that, when in a supercritical state, can complex with $O_2$. By forming a complex with the $O_2$, the supercritical electron donor solvent can facilitate conversion of methane to methanol at short residence times while reducing or minimizing further oxidation of the methanol to other products. It is noted that sub-critical conditions (either pressure or temperature below the critical point) do not appear to lead to the increased oxidation of methane to methanol as described herein.

In various aspects, it has further unexpectedly been discovered that the conversion of methane to methanol in the presence of $O_2$ can be improved or facilitated by decreasing the available oxygen content for oxidation. Conventionally, the relative concentration of methane to $O_2$ in the reaction environment has represented a trade-off between increased conversion (of any type) of methane versus increased additional oxidation of methanol (after initial conversion) to other products. Conventionally, this trade-off has limited the yield of methanol to less than 1 mole % relative to the molar amount of $O_2$ in the reaction environment.

By contrast, the methods described herein related to using an electron donor solvent under supercritical conditions can allow for increased conversion of methane based on decreasing the ratio of methane to $O_2$. Without being bound by any particular theory, it is believed that the supercritical solvent reaction environment can provide solvent clusters for activation of $O_2$ (via specific solute-solvent interactions) to enable methane oxidation while expanding the residence time window for increased or improved recovery of methanol as the oxidation product. Based on the increased reactivity of the activated $O_2$, it is believed that the residence time window for recovery of methanol can be further increased by decreasing the concentration of $O_2$, while still providing an overall improvement in yield of methanol relative to the amount of oxygen in the reaction environment. This improved yield relative to the amount of oxygen can provide other potential benefits, such as potentially improving the yield relative to the amount of methane and/or reducing or minimizing the loss of methane to other conversion products (i.e., increasing the selectivity of the conversion reaction for producing methane). In various aspects, the molar ratio of methane to $O_2$ can be 2.0 or more, or 4.0 or more, or 8.0 or more, or 15 or more, such as up to 50 or possibly still higher.

The electron donor solvent can correspond to a non-aqueous solvent. Although water may be present, it is undesirable from both a reaction standpoint and from a product recovery standpoint to have excess water in the reaction environment. From a reaction standpoint, water typically serves as a proton donor/electron acceptor, and therefore is not suitable for playing a role as an electron donor solvent. From a product recovery standpoint, methanol is miscible in water and is difficult to fully recover using simple distillation. Thus, it can be beneficial to form methanol in a reaction environment that has a reduced or minimized amount of water. In various aspects, water can correspond to 10 mole % or less of the reaction environment, or 1.0 mole % or less, or 0.1 mole % or less, such as down to having substantially no water content (0.01 mole % or less). The amount of water can preferably be less than the amount of the electron donor solvent.

Instead of using water, examples of electron donor solvents can include solvents such as $CO_2$, acetonitrile, and various halogenated derivatives of acetonitrile. It is noted that $CO_2$ and acetonitrile may sometimes be referred to as examples of weak electron donor solvents. In addition to being electron donors, these examples of electron donor solvents also have a critical point temperature of about 310° C. or less, or about 300° C. or less, or about 290° C. or less. In various aspects, improved yields of methanol from methane can be achieved in an electron donor solvent at supercritical conditions. However, at temperatures of about 300° C. or more, methanol can readily oxidize to $CO_2$ and $H_2O$ in the presence of an oxidant. Maintaining the reaction environment at supercritical conditions while staying below about 310° C., or below about 300° C., or below about 290° C., can facilitate oxidation of methane to methanol while reducing or minimizing the direct oxidation of the methanol to $CO_2$. In various aspects, relative to the total moles of conversion products, the selectivity for $CO_2$ production can be 50 mole % or less, or 30 mole % or less, or 20 mole % or less, such as down to 1 mole % or possibly still lower.

In various aspects, oxidizing methane to methanol in a supercritical solvent corresponding to an electron donor can allow for methanol yields, relative to oxygen ($O_2$) present in the reaction environment, of 1.0 mole % or more, or 2.0 mole % or more, or 5.0 mole % or more, or 10 mole % or more, such as up to 25 mole % or possibly still higher. The molar ratio of solvent to oxygen in the reaction environment can optionally but preferably be 5.0 or more, or 8.0 or more, such as up to 50 or possibly still higher. It is noted that in some aspects, air can be a convenient source of $O_2$. The upper limit on the molar ratio of solvent to oxygen can be related to practical issues, such as being able to perform the reaction without requiring excessive volumes for the reaction environment. In various aspects, oxidizing methane to methanol in a supercritical solvent corresponding to an electron donor can allow for methanol yields, relative to methane present in the reaction environment, of 0.7 mole % or more, or 0.9 mole % or more, or 1.2 mole % or more, such as up to 3.5 mole % or possibly still higher.

Acetonitrile is an example of a suitable solvent for use at supercritical conditions for oxidation of methane to methanol. The supercritical temperature and pressure for acetonitrile are 272° C. and 4.87 MPa-a.

In some aspects, a minor amount of an initiator can be used to further increase the yield of oxygen. Examples of initiator compounds can include boron nitride and hydrogen peroxide. Initiator compounds can be included in the reaction environment in sub-stoichiometric amounts. For example, the molar amount of initiator can be 70% or less relative to the molar amount of oxygen, or 50% or less, or 30% or less, or 10% or less, such as down to 1% or possibly still lower. Additionally or alternately, where the initiator corresponds to a solid compound such as boron nitride, a comparison of stoichiometric amounts may not be the appropriate comparison. For example, boron nitride typically can have a surface area of less than 100 $m^2/g$, so that the available surface area for serving as an initiator may be relatively low, even though the net weight and/or moles of boron nitride in a reaction environment is relatively high.

It is noted that $C_{2+}$ hydrocarbons can typically be susceptible to oxidation under milder conditions than methane. In some aspects, the reaction environment can include other hydrocarbons (i.e., $C_{2+}$ hydrocarbons) that can also be oxidized during the conversion of methane to methanol. In other aspects, the reaction environment can be substantially free of $C_{2+}$ hydrocarbons, so as to reduce or minimize competing side reactions to form oxygenated $C_{2+}$ side products. A reaction environment that is substantially free of $C_{2+}$ hydrocarbons can correspond to a reaction environment where the molar amount of $C_{2+}$ hydrocarbons is less than 1% of the molar amount of methane, or less than 0.1%.

Definitions

In this discussion, direct conversion of methane to methanol is defined as a conversion process where the exposure of the methane to a single reaction environment results in production of methanol. This is in contrast to indirect conversion methods, where two or more reaction environments are used. In a first reaction environment, methane is converted to one or more intermediates, and then the intermediate(s) are converted in a second reaction environment that has one or more differences relative to the first reaction environment. The one or more differences can correspond to a difference in temperature of at least 5% (relative to the temperature in Kelvin of the first environment); a difference in pressure of at least 5%; the presence of absence of a catalyst; the presence or absence of a reagent; or a combination thereof.

In this discussion, substantially supercritical conditions for a solvent are defined as conditions where one of the temperature and pressure of the reaction environment are beyond the critical point, while the other of the temperature and pressure are within 5 percent of the critical point. For instances where the pressure is beyond the critical point pressure, the temperature can be different from the critical point temperature by less than 5% (in Kelvin).

In this discussion, a reaction environment is defined as a contiguous volume that has supercritical conditions for the solvent.

In this discussion, a solvent refers to a compound present in the reaction environment a) that is present in a molar amount that is greater than the molar amount of oxygen, and b) that is not consumed during the oxidation reaction to convert methane to methanol. Thus, a solvent corresponds to a compound that is substantially non-reactive under in the reaction environment under conditions where the solvent is supercritical. Examples of solvents include, but are not limited to, acetonitrile, carbon dioxide, tricholoroacetonitrile, fluoroacetonitrile, trifluoroacetonitrile, and combinations thereof.

In this discussion, the residence time can refer to the average amount of time that methane is exposed to oxygen under supercritical conditions or under at least one of supercritical conditions and substantially supercritical conditions. In various aspects, the residence time can correspond to 10 minutes or less, or 1.0 minutes or less, or 0.1 minutes or less. In various aspects, the residence time can correspond to 0.1 seconds or more, or 1.0 seconds or more, or 10 seconds or more, or 1.0 minutes or more. In some aspects, the residence time a) under supercritical conditions or b) under at least one of supercritical conditions and substantially supercritical conditions can be 0.1 seconds to 10 minutes, or 0.1 seconds to 1.0 minutes, or 1.0 seconds to 1.0 minutes, or 10 seconds to 10 minutes, or 10 seconds to 1.0 minutes.

Cluster Formation and Supercritical Solvent

Without being bound by any particular theory, it is believed that using a supercritical electron donor solvent can facilitate oxidation of methane to methanol by forming complexes with the $O_2$. The complexes can potentially provide several benefits. One type of benefit can correspond to activation of $O_2$ molecules. For example, it is believed that $O_2$ molecules can interact with clusters of solvent molecules and become partially polarized. This partial polarization can facilitate breaking the $O_2$ bond so that the $O_2$ can react with methane to form methanol. Additionally or alternately, another type of benefit can correspond to modulating the local concentration of $O_2$. Conventionally, one of the difficulties with oxidizing methane with $O_2$ is stopping the oxidation reaction at methanol. Under conventional conditions for methane oxidation, once methane starts the oxidation process, the reaction products can tend to oxidize past methanol to another product, such as formaldehyde or $CO_2$. Without being bound by any particular theory, it is believed that the association of $O_2$ with the solvent clusters can reduce or minimize local concentration variations. This can increase the residence time window where methanol can be formed and then removed from the reaction environment without further oxidation to other products.

It is believed that the ability to form reduced or minimized energy solvent clusters can contribute to the ability to activate oxygen and/or moderate oxygen concentration variations within the solvent environment. It is further believed that this cluster formation can be enhanced by using a solvent under supercritical conditions. Under supercritical conditions, the phase boundary between a liquid phase and a gas phase is not present. Instead, a continuous fluid phase is present beyond the supercritical point for a solvent. The absence of a gas-liquid phase transition is indicative of a fluid state where individual molecules are close enough together to form clusters while having sufficient energy to escape local minima and potentially spend substantial time in cluster states with favorable energy.

In order to further investigate the interaction of solvent clusters and oxygen, density functional calculations were performed on a variety of solvent clusters. The calculations corresponded to density functional theory (DFT) calculations performed at the B3LYP/6-311++G(d,p), to determine local energy minima for various cluster sizes (2-16 molecules) of acetonitrile compounds. After determining the lowest energy configurations at the various cluster sizes, dipole moments for each cluster were determined. The results of the calculations are shown in Table 1, along with the corresponding dipole moment calculated by DFT for a single acetonitrile molecule.

TABLE 1

Dipole Moment of Optimized Acetonitrile Clusters

| Cluster size, n | Dipole moment (Debye) |
|---|---|
| CH3CN (n = 1) | 4.0534 |
| $(CH3CN)_2$ (n = 2) | 0.001 |
| $(CH3CN)_3$ (n = 3) | 0.0026 |
| $(CH3CN)_4$ (n = 4) | 0.0005 |
| $(CH3CN)_5$ (n = 5) | 0.2028 |
| $(CH3CN)_6$ (n = 6) | 0.0016 |
| $(CH3CN)_8$ (n = 8) | 0.0134 |
| $(CH3CN)_{12}$ (n = 12) | 1.0243 |
| $(CH3CN)_{16}$ (n = 16) | 0.0544 |

As shown in Table 1, with the exception of the n=12 cluster, the dipole moment for the lowest energy cluster for each cluster size was close to zero. This is in contrast to the dipole moment of roughly 4 Debye for a single acetonitrile cluster. Without being bound by any particular theory, it is believed that under supercritical conditions, the molecular configurations for an acetonitrile solvent include a substantial contribution from minimum energy clusters that also have a reduced or minimized dipole moment.

Additional DFT calculations were performed for incorporation of an $O_2$ molecule into acetonitrile clusters. In Table 2, results are shown from determining minimum energy configurations for $O_2$ in a cluster including n=4, 5, or 6 acetonitrile molecules. The configuration for the acetonitrile molecules at the start of optimization roughly corresponded to the minimum energy configuration for the cluster without the presence of $O_2$. The results in Table 2 show the charge on each oxygen atom in the $O_2$ molecule when incorporated into the n=4, 5, or 6 clusters.

TABLE 2

Charge on Oxygen Atoms for $O_2$ in Acetonitrile Clusters

| Cluster-O2 | Charge on Oxygen1 | Charge on Oxygen2 |
|---|---|---|
| $(CH3CN)_4$—$O_2$ | 0.08 | −0.03 |
| $(CH3CN)_5$—$O_2$ | 0.095 | −0.029 |
| $(CH3CN)_6$—$O_2$ | 0.07 | −0.02 |

As shown in Table 2, incorporation of $O_2$ into the acetonitrile clusters resulted in an asymmetric charge distribution between the oxygen atoms in the $O_2$. It is believed that this polarization of the $O_2$ can contribute to activation of the $O_2$ for reaction with methane to form methanol. With regard to details for the minimum energy configurations, in the tetramer (n=4) and pentamer (n=5) clusters, the $O_2$ was interacting with 2 of the hydrogen bonded interactions in the acetonitrile clusters (i.e., an interaction between C—H at one end of a first molecule and N from a second molecule) leading to polarization of $O_2$. In the case of the hexamer cluster (n=6), oxygen was interacting via hydrogen bonds with hydrogens that were not involved in intermolecular interactions of the hexamer cluster.

Example Configuration

To illustrate the benefits of performing methane oxidation to methanol at supercritical solvent conditions, a test apparatus was constructed. In the test apparatus, a reactor controller (such as a controller that includes a PID controller) was used to control the temperature in a reactor via a heater. The reactor corresponded to a reactor that was suitable as a reaction environment at temperatures of up to roughly 300° C. and pressures of up to roughly 15 MPa-g. An example of a suitable reactor is a high pressure reactor (50 mL) available from Parr Instruments. The reactor vessel included inputs for introducing gases from a nitrogen source, an oxygen source, and a methane source. Any other components in the reaction environment (such as solvent and/or initiator) were introduced into the reactor directly prior to sealing the reactor. The reactor controller monitored the conditions in the reactor via a thermocouple and a pressure sensor. Optionally, a helium source could have been used in place of or in addition to the nitrogen source. The system further included a liquid nitrogen source to allow for cooling of the reactor during introduction of the oxygen and methane into the reaction environment.

In a typical reaction, solvent and any optional catalyst/initiator/other reagents were loaded to the reactor. The reactor was then cooled down to −35° C. by use of liquid nitrogen and pressurized with desired amount of $O_2$, $CH_4$ and neutral gas ($N_2$ or He) while the temperature was stable at −35° C. Then the reactor was heated to a temperature in the range of 250° C.-300° C., or 275° C.-300° C., with a ramp rate of 2.5° C./min and the desired dwelling time. The dwelling time at the final temperature was typically either 0 minutes (no dwell time) or 3 minutes. The reactor was then cooled down to ambient temperature by natural convection. The products were analyzed by GC-MS (gas chromatography-mass spectrometry) and NMR to determine methanol concentration. It is noted that the reactor described herein corresponded to a batch reactor. However, the reactions described herein can alternatively be performed in a continuous reaction environment. It is further noted that the benefits of low dwell time shown below can in some ways be more readily achieved in a continuous reaction environment.

Example 1—Oxidation Under Supercritical Solvent Conditions

The experimental procedure described above was used to expose methane to $O_2$ in the presence of acetonitrile as a solvent under various conditions as shown in Table 3. 3 mL (57 mmol) of acetonitrile was loaded into the reactor. $CH_4$, $O_2$, and $N_2$ were then fed into the reactor at a temperature of −35° C. The amount of $CH_4$ was 77 mmol while the $O_2$ was 19 mmol. This corresponded to a molar ratio of $CH_4$ to $O_2$ of roughly 3.8. $N_2$ was then added to provide roughly the desired pressure when the final temperature of 300° C. was reached. As shown in Table 3, the pressure and temperature were varied to perform the experiment under conditions that corresponded to supercritical acetonitrile, substantially supercritical acetonitrile, and traditional gas or liquid phase acetonitrile. The methanol yield corresponds to moles of methanol produced relative to moles of $O_2$ in the reaction environment.

TABLE 3

Methane Oxidation in Supercritical and Sub-Supercritical Acetonitrile

| Phase | Pressure (MPa-a) | T (° C.) | MeOH Yield (mol %) |
|---|---|---|---|
| Ambient | 0.1 | 300 | 0 |
| Subcritical | 2.8 | 300 | 0 |
| Supercritical | 5.6 | 300 | 1.0 |
| Supercritical | 8.4 | 300 | 1.5 |
| Supercritical | 8.4 | 275 | 1.3 |
| Subcritical | 8.4 | 250 | 0.1 |

As shown in Table 3, the first two pressure and temperature combinations were at pressures below the critical point for acetonitrile (less than 4.87 MPa-a), while the final condition was at a temperature below the critical point for acetonitrile (272° C.). At pressures below the critical point, no methanol formation was observed. At substantially supercritical combination of 8.4 MPa-a and 250° C., a small amount of methanol formation was observed. However, the amount of methanol yield was an order of magnitude lower than the methanol yield for the supercritical conditions.

It is noted that some of the supercritical conditions shown in Table 3 were repeated using fully deuterated acetonitrile ($CD_3CN$). When using fully deuterated acetonitrile, no deuterium was incorporated into the methanol product. This indicates that the supercritical solvent was facilitating the reaction without serving as a reagent.

Example 2—Methane to Oxygen Ratio

In this example, 3 mL (57 mmol) of acetonitrile loading to the reactor and cold fed (−35° C.) with desired $O_2$, $CH_4$ and sufficient neutral gas to achieve a target pressure of 10 of roughly 10 MPa-a at −35° C. This resulted in pressures of roughly 28 MPa-a at the final temperature of 300° C. The amounts of $O_2$ and $CH_4$ were varied as shown in Table 4 to provide various molar ratios of $CH_4:O_2$. The reactor was then heated with a ramp rate of 2.5° C./min up to 300° C. and then cooled to ambient (no dwell time) at natural convection rate. In Table 4, the methanol yield is reported as a yield relative to both the moles of $O_2$ and the moles of $CH_4$. The resulting molar concentration of $CH_3OH$ in the reactor was also determined. It is noted that multiple tests were performed at some reaction conditions. For conditions were several test results were available, the results were averaged and error bars were calculated for the result.

TABLE 4

Methane to Oxygen Ratio

| $CH_4$ (mmol) | $O_2$ (mmol) | Ratio of $CH_4:O_2$ | MeOH yield (%) $O_2$ based | MeOH yield (%) $CH_4$ based | MeOH Concentration (M) |
|---|---|---|---|---|---|
| 11 | 22 | 0.5 | 0.1 | 0.3 | 0.01 |
| 71 | 19 | 3.7 | 2.6 | 1.4 | 0.33 |
| 118 | 13.5 | 8.7 | 4.1 | 0.94 | 0.37 |
| 118 | 7 | 16.8 | $6^{+/-0.8}$ | 0.71 | 0.28 |
| 181 | 3 | 60.3 | 5.0 | 0.16 | 0.1 |

As shown in Table 4, increasing the molar ratio of $CH_4$ to $O_2$ resulted in increased amounts of methanol formation for ratios up to roughly 9:1 or 10:1. At $CH_4$ to $O_2$ molar ratios greater than 15:1, the yield relative to $O_2$ may still be higher, but the relative lack of $O_2$ in the environment means that the yield relative to $CH_4$ starts to decline for molar ratios greater than about 5:1. At molar ratios of 15:1 or higher, the decline in methanol yield can also cause the net concentration of methanol reaction environment after conversion to be lower.

It is noted that all of the methanol yields about 1.0 mol % relative to the amount of $O_2$ are unexpectedly high. Conventionally, reducing the amount of $O_2$ would be expected to a decrease in both conversion to methanol and conversion to any type of product, with yield relative to amount of $O_2$ being relatively constant. By contrast, it is believed that the supercritical solvent environment can activate $O_2$ for reaction so that high yields of methanol can be generated while reducing or minimizing the production of other oxidation products, such as $CO_2$.

Example 3—Temperature Variations

This example provides additional illustration of the impact of temperature on the oxidation reaction. 3 mL of acetonitrile was loaded to the reactor and then gases were cold fed at −35° C., including 7 mmol of $O_2$, 118 mmol of $CH_4$ and 163 mmol of neutral gas (He or $N_2$). The pressure in the reactor after loading the gases at −35° C. was roughly 10 MPa-a. The reactor was then heated at a 2.5° C./min ramp rate to achieve the target temperature shown in Table 5. This resulted in an increase in the reactor pressure. The pressure values shown in Table 5 correspond to the calculated pressures based on an ideal gas law calculation, using the initial pressure at −35° C. as the basis for determining the final pressure in the constant reactor volume. After heating to the target temperature, the reactor was allowed to cool by natural convection without dwell time at the target temperature.

TABLE 5

Temperature Dependence of Conversion

| Pressure | T (° C.) | MeOH yield ($CH_4$ basis) | MeOH yield ($O_2$ basis) | $CO_2$ selectivity | $O_2$ conversion |
|---|---|---|---|---|---|
| 26.9 MPa-a | 250 | 0.04 | 0.3 | 50 | 0.8 |
| 28.3 MPa-a | 275 | 0.5 | 4.6 | 15 | 5.4 |
| 29.6 MPa-a | 300 | 0.72 | $6^{+/-0.8}$ | 80 | 30 |

In addition to methanol yield relative to moles of $CH_4$ or $O_2$ in the reaction environment, Table 5 also provides $CO_2$ selectivity (yield) relative to $CH_4$ and $O_2$ conversion. As shown in Table 5, at the substantially supercritical conditions including a temperature of 250° C., only a modest amount of methanol was formed. The amount of $CO_2$ formed was comparable to or greater than the amount of methanol, but the main result was that little or no conversion of any type is occurring. This was confirmed by the relatively small percentage of $O_2$ that was converted. At 275° C., so that the acetonitrile was supercritical, the methanol yield was higher and the amount of $CO_2$ formed corresponded to only 15 vol % of the reaction products. Under these conditions, the yield of methanol versus other products is believed to be relatively high. Further increasing the temperature to 300° C. results in additional methanol production, but the majority of the conversion product (80 vol %) corresponds to $CO_2$. Thus, even though more methanol is being produced, a substantial amount of $CH_4$ and $O_2$ were converted to $CO_2$, as opposed to being available for processing again under the reaction conditions. Depending on the availability of methane, it could be a desirable trade-off to improve single-pass conversion rate in exchange for additional conversion of methane to $CO_2$ (and/or other non-methanol oxidation products).

Example 4—Solvent to Oxygen Ratio

This example illustrates the impact of the solvent to oxygen ratio in the reaction environment. 3 mL of acetonitrile was loaded into the reactor and then gases were cold fed at −35° C., including 163 mmol of He gas loading, 113-124 mmol $CH_4$ loading, and 6.7-7.4 mmol of $O_2$. The pressure in the reactor after loading the gases at −35° C. was roughly 10 MPa-a. The reactor was then heated at a 2.5° C./min ramp rate to achieve a target temperature of 275° C. After heating to the target temperature, the reactor was allowed to cool by natural convection without dwell time at the target temperature. Table 6 shows the results at the different solvent to oxygen molar ratio values. As shown in Table 6, the $CH_4$ to $O_2$ molar ratio is roughly 16:1.

TABLE 6

Solvent to Oxygen Ratio

| MeCN (mmol) | $CH_4$ (mmol) | $O_2$ (mmol) | Ratio of Solvent:$O_2$ | MeOH yield (%) $O_2$ based |
|---|---|---|---|---|
| 10 | 124 | 7.4 | 1.3 | 0.2 |
| 20 | 123 | 7.3 | 2.6 | 0.6 |
| 38 | 120 | 7.3 | 5.2 | 3 |
| 57 | 118 | 7.3 | 8 | 4.6 |

As shown in Table 6, at solvent:$O_2$ ratios near 1, the amount of solvent appears to be insufficient to activate the $O_2$ for the oxidation reaction. Increasing the solvent:$O_2$ ratio to 2.6 results in some additional activity. However, the improved yields of methanol relative to the amount of oxygen were not observed until the molar ratio of solvent to $O_2$ was greater than about 5. Further increases in the solvent to $O_2$ ratio resulted in additional methanol yield relative to the amount of oxygen.

Example 5—Solvent Type

This example provides an illustration of the impact of the nature of the solvent on the oxidation reaction. Instead of using only acetonitrile as a solvent, a series of different solvents was used. In this example, the reaction conditions corresponded to a temperature of 275° C. or 300° C., with a pressure of roughly 28 MPa-a. This was sufficient to provide supercritical conditions for acetonitrile and the acetonitrile derivatives and $CO_2$. However, the critical point of water is roughly 375° C. Due to the known oxidation pathway for methanol to convert to $CO_2$ rapidly at temperatures greater than 300° C., it was decided that the better comparison was to compare with water as a solvent at the same temperature, as increasing the temperature sufficiently to form supercritical water would be expected to result in substantially no methanol production (i.e., all methanol would be converted to $CO_2$).

For the acetonitrile and deuterated acetonitrile runs shown in Table 7, 3 mL of solvent was loaded into the reactor along with 7 mmol of $O_2$, 118 mmol of $CH_4$ and 163 mmol of neutral gas (He or $N_2$) at −35° C. The reactor was then heated at a 2.5° C./min ramp rate up to 300° C., followed by cooling (zero dwell time) back to ambient via natural convection.

For fluoroacetonitrile as the solvent, 17 mmol of solvent was loaded to the reactor along with 7 mmol of $O_2$, 118 mmol of $CH_4$ and 163 mmol of neutral gas (He or $N_2$) at −35° C. The reactor was then heated at a 2.5° C./min ramp rate up to 300° C., followed by cooling (zero dwell time) back to ambient via natural convection.

For trichloroacetonitrile as a solvent, a mixture of trichloroacetonitrile in acetonitrile in 1:10 ratio, corresponding to a total of 3 mL solution, was loaded into the reactor. The gases were then cold fed at −35° C., including 7 mmol of $O_2$, 118 mmol of $CH_4$ and 163 mmol of neutral gas (He or $N_2$). The reactor was then heated at a 2.5° C./min ramp rate up to 300° C., followed by cooling (zero dwell time) back to ambient via natural convection.

For water as a solvent, 3 mL of water was loaded into the reactor and gases were cold fed into the reactor at −35° C. corresponding to 22 mmol of $O_2$, 72 mmol of $CH_4$, and 114 mmol of $N_2$. The reactor was then heated at about 2.5° C./min ramp rate up to 300° C. The reactor was then allowed to dwell at 300° C. for roughly 3 hours, followed by cooling back to ambient via natural convection.

For $CO_2$ as the solvent, 118 mmol of $CH_4$, 7 mmol of $O_2$, 57 mmol of $CO_2$, and 103 mmol of He were cold fed into the reactor at −35° C. The reactor was then heated up to 275° C. at a roughly 2.5° C./min ramp rate (zero dwell time), followed by cooling to ambient via natural convection.

TABLE 7

Solvent Effect on Stabilization of Product

| Solvent | MeOH yield (%) $O_2$ based |
|---|---|
| MeCN | 6 |
| Deuterated Acetonitrile | 3 |
| Fluoroacetonitrile | 4 |
| Trichloroacetonitrile | 1 |
| Water | 0.4 |
| $CO_2$ | 0.5 |

As shown in Table 7, all of the acetonitrile derivatives provided improved methanol yield, relative to the molar amount of $O_2$, in comparison with using water at elevated pressure and temperature.

Example 6—Boron Nitride as an Initiator

It has been unexpectedly discovered that the yield of methanol can be further enhanced by using boron nitride as an initiator. Table 8 shows results from use of boron nitride with various amounts of acetonitrile solvent. In the runs shown in Table 8, the desired amount of acetonitrile was loaded into the reactor along with 200 mg of boron nitride. Then gases were cold fed at −35° C., including 7 mmol of $O_2$, 118 mmol of $CH_4$ and 163 mmol of neutral gas (He or $N_2$). The reactor was then heated up to 275° C. at a roughly 2.5° C./min ramp rate (zero dwell time), followed by cooling to ambient via natural convection.

TABLE 8

Boron Nitride as an Initiator

| MeCN (mmol) | Stirring (rpm) | MeOH yield (%) $O_2$ based |
|---|---|---|
| 57 | 0 | 5.2 |
| 57 | 60 | 7.8 |
| 0 | 60 | 3 |

It is noted that 57 mmol of acetonitrile corresponds to the typical amount added in most of the examples, and provided a solvent to $O_2$ molar ratio of roughly 8:1. As shown in Table 8, addition of boron nitride as an initiator without stirring resulted in a modest increase of methanol yield from roughly 4.6 mole % to roughly 5.2 mole % relative to the amount of $O_2$. (Compare, for example, with final row of Table 6 or middle row of Table 5.) With stirring, the methanol yield increased to 7.8 mole %. It is noted that even without the presence of the acetonitrile solvent, the boron nitride initiator was able to generate a 3 mole % yield of methanol relative to the amount of $O_2$. This is in contrast to the first row of Table 6, which showed little or substantially no conversion at a solvent to $O_2$ ratio of roughly 1.0.

Example 7—Methanol Yield Versus Dwell Time

This example provides an illustration of the impact of the nature of the solvent on the oxidation reaction. Additionally, the impact of including a copper-containing catalyst was also studied.

In this example, 3 mL of acetonitrile was loaded into the reactor. The reactor was cold fed with 22 mmol of $O_2$, 72 mmol of $CH_4$, and 114 mmol of $N_2$. The gases were fed at −35° C. including 28 mmol of $O_2$, 100 mmol of $CH_4$, and 160 mmol of $N_2$. The reactor was then heated at about 2.5° C./min ramp rate up to 300° C. The reactor was then allowed to cool immediately (no dwell time), or the reactor remained heated for the desired dwell time followed by cooling. Table 9 shows the variation in methanol yield based on dwell time.

TABLE 9

Methanol Yield versus Dwell Time

| System | Dwell time (h) | MeOH yield (%) $O_2$ based |
|---|---|---|
| Acetonitrile | 3 | 0.1 |
| Acetonitrile | 0 | 1.5 |

As shown in Table 9, allowing the reactor to remain at the supercritical conditions for an extended period of time resulted in a substantial loss in methanol yield.

ADDITIONAL EMBODIMENTS

Embodiment 1

A method for partial oxidation of methane comprising: contacting methane with $O_2$ in the presence of a solvent in a reaction environment under supercritical conditions for the solvent to form methanol, the supercritical conditions comprising a temperature of 310° C. or less.

Embodiment 2

The method of Embodiment 1, wherein the solvent comprises an electron donor solvent.

Embodiment 3

The method of Embodiment 2, wherein the electron donor solvent comprises acetonitrile, carbon dioxide, tricholoroacetonitrile, fluoroacetonitrile, trifluoroacetonitrile, or a combination thereof; or wherein the electron donor solvent comprises acetonitrile, carbon dioxide, or a combination thereof.

Embodiment 4

The method of any of the above embodiments, wherein the $O_2$ is contacted with the methane under the supercritical conditions for a residence time of 10 minutes or less, or 1.0 minutes or less; or wherein the $O_2$ is contacted with the methane under at least one of supercritical conditions and substantially supercritical conditions for a residence time of 10 minutes or less, or 1.0 minutes or less; or a combination thereof.

Embodiment 5

The method of any of the above embodiments, wherein the $O_2$ is contacted with the methane under at least one of supercritical conditions and substantially supercritical conditions for a residence time of 0.1 seconds or more, or 1.0 seconds or more, or 10 seconds or more.

Embodiment 6

The method of any of the above embodiments, wherein the reaction environment comprises 10 mole % or less of $H_2O$, or 1.0 mole % or less, or 0.1 mole % or less.

Embodiment 7

The method of any of the above embodiments, wherein the yield of methanol is 1.0 mole % or more relative to the molar amount of $O_2$ in the reaction environment, or 2.0 mole % or more, or 5.0 mole % or more, or 10.0 mole % or more; or wherein the yield of methanol is 0.7 mole % or more relative to the molar amount of $CH_4$ in the reaction environment, or 0.9 mole % or more, or 1.2 mole % or more; or a combination thereof.

Embodiment 8

The method of any of the above embodiments, wherein the supercritical conditions comprise a temperature of 300° C. or less, or 290° C. or less.

Embodiment 9

The method of any of the above embodiments, wherein contacting the methane with $O_2$ further comprises contacting the methane with $O_2$ in the presence of an initiator.

Embodiment 10

The method of Embodiment 9, a) wherein the molar amount of the initiator in the reaction environment is 70% or less than the molar amount of $O_2$, or 50% or less, or 30% or less; b) wherein the initiator comprises boron nitride, hydrogen peroxide, or a combination thereof; or c) a combination of a) and b).

Embodiment 11

The method of any of the above embodiments, wherein the reaction environment further comprises one or more $C_{2+}$ hydrocarbons.

Embodiment 12

The method of any of the above embodiments, wherein the reaction environment is substantially free of $C_{2+}$ hydrocarbons.

Embodiment 13

The method of any of the above embodiments, wherein the molar ratio of solvent to $O_2$ is 5.0 or more, or 8.0 or more; or wherein the molar ratio of methane to $O_2$ is 2.0 or more, or 4.0 or more, or 8.0 or more, or 15 or more; or a combination thereof.

Embodiment 14

The method of any of the above embodiments, wherein the selectivity for $CO_2$ is 50 mole % or less relative to total moles of conversion products, or 30 mole % or less, or 20 mole % or less.

Embodiment 15

A methanol-containing product formed according to the method of any of Embodiments 1 to 14.

All patents, test procedures, and other documents cited herein, including priority documents, are fully incorporated by reference to the extent such disclosure is not inconsistent with this invention and for all jurisdictions in which such incorporation is permitted. Should the disclosure of any of the patents and/or publications that are incorporated herein by reference conflict with the present specification to the extent that it might render a term unclear, the present specification shall take precedence.

As should be apparent from the foregoing general description and the specific embodiments, while forms of the invention have been illustrated and described, various modifications can be made without departing from the spirit and scope of the invention. Accordingly, it is not intended that the invention be limited thereby. Many variations will suggest themselves to those skilled in this art in light of the above detailed description. All such variations can be within the full intended scope of the appended claims. Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

The invention claimed is:

1. A method for partial oxidation of methane comprising:
contacting methane with O2 in the presence of a solvent, but in the absence of a catalyst, in a reaction environment under supercritical conditions for the solvent to form methanol, the supercritical conditions comprising a temperature of about 250° C. and about 310° C.

2. The method of claim 1, wherein the solvent comprises an electron donor solvent.

3. The method of claim 2, wherein the electron donor solvent comprises acetonitrile, tricholoroacetonitrile, fluoroacetonitrile, trifluoroacetonitrile, or a combination thereof.

4. The method of claim 2, wherein the solvent comprises acetonitrile.

5. The method of claim 1, wherein the O2 is contacted with the methane under the supercritical conditions for a residence time of 10 minutes or less.

6. The method of claim 1, wherein the O2 is contacted with the methane under at least one of supercritical conditions and substantially supercritical conditions for a residence time of 10 minutes or less.

7. The method of claim 1, wherein the O2 is contacted with the methane under at least one of supercritical conditions and substantially supercritical conditions for a residence time of 0.1 seconds or more.

8. The method of claim 1, wherein the reaction environment comprises 10 mole % or less of $H_2O$.

9. The method of claim 1, wherein the yield of methanol is 1.0 mole % or more relative to the molar amount of $O_2$ in the reaction environment.

10. The method of claim 1, wherein the yield of methanol is 0.7 mole % or more relative to the molar amount of $CH_4$ in the reaction environment.

11. The method of claim 1, wherein the supercritical conditions comprise a temperature of about 250° C. and about 300° C.

12. The method of claim 1, wherein contacting the methane with $O_2$ further comprises contacting the methane with $O_2$ in the presence of an initiator.

13. The method of claim 12, wherein the molar amount of the initiator in the reaction environment is 70% or less than the molar amount of $O_2$.

14. The method of claim 12, wherein the initiator comprises boron nitride, hydrogen peroxide, or a combination thereof.

15. The method of claim 1, wherein the reaction environment further comprises one or more C2+ hydrocarbons.

16. The method of claim 1, wherein the reaction environment is substantially free of C2+ hydrocarbons.

17. The method of claim 1, wherein the molar ratio of solvent to $O_2$ is 5.0 or more.

18. The method of claim 1, wherein the molar ratio of methane to $O_2$ is 2.0 or more.

19. The method of claim 1, wherein the selectivity for $CO_2$ is 50 mole % or less relative to total moles of conversion products.

* * * * *